United States Patent [19]
Thompson et al.

[11] Patent Number: 5,492,817
[45] Date of Patent: *Feb. 20, 1996

[54] COUPLED TRANSCRIPTION AND TRANSLATION IN EUKARYOTIC CELL-FREE EXTRACT

[75] Inventors: David V. Thompson, Monona; Thomas R. Van Oosbree, Madison; Gregory S. Beckler, Portage; John F. Van Herwynen, Stoughton, all of Wis.

[73] Assignee: Promega Corporation, Madison, Wis.

[ * ] Notice: The term of this patent shall not extend beyond the expiration date of Pat. No. 5,224,637.

[21] Appl. No.: 266,228

[22] Filed: Jun. 27, 1994

Related U.S. Application Data

[63] Continuation of Ser. No. 149,715, Nov. 9, 1993, Pat. No. 5,324,637.

[51] Int. Cl.$^6$ .................................................. C12P 21/00
[52] U.S. Cl. ...................... 435/68.1; 435/69.1; 435/320.1
[58] Field of Search .................................. 435/68.1, 69.1, 435/320.1

[56] References Cited

U.S. PATENT DOCUMENTS 5,324,637  6/1994  Thompson .............................. 435/68.1

OTHER PUBLICATIONS

Zubay, G. (1973) *Ann. Rev. Genet.* vol. 7, p. 267.
Pelham, H. R. B. and Jackson, R. J. (1976) *Eur. J. Biochem.* vol. 67, p. 247.
Walter, P. and Biobel, G. (1983) *Meth. Enzymol.* 96, 84.
Glass, C. A. and Pollard, K. M. (1990) *Promega Notes* 26.
Roberts, B. E. and Paterson, B. M. (1973) *Proc. Natl. Acad. Sci. USA*, vol. 70, p. 2330.
Anderson, C., et al. (1983) *Meth. Enzymol.* 101, 635.
Krieg, P. and Melton, D. (1984) *Nucl. Acids Res.*, vol. 12, p. 7057.
Roberts, B. E., et al. (1975) *Proc. Natl. Acad. Sci. USA*, vol. 72, 1922–1926.

Pelham, H. R. B., et al. (1978), *Eur. J. Biochem.*, vol. 82, 199–209.

Spirin, et al. (1988) *Science*, vol. 242, 1162–1164.

Ryabova, et al. (1989) *Nucl. Acid Res.*, vol. 17, No. 11, 4412.

Baranov, et al. (1989) *Gene*, vol. 84, 463–466.

Manufacturing Protocol L418, Promega Corp., Madison, Wis.

Technical Bulletin 101, Promega Corp., Madison, Wis.

*in vitro* Translation Technical Manual, Promega Corp., Madison, Wis.

Manufacturing Protocol L415/L416, Promega Corp., Madison, Wis.

Jackson, R. and Hunt, T. (1983) *Meth. In Enzymol.* 96, 50.

Suzuki (1977) *J. Biochem.* vol. 82, 251–260.

*Primary Examiner*—Mindy Fleisher
*Assistant Examiner*—David Schmickel
*Attorney, Agent, or Firm*—Michael, Best & Friedrich

[57] ABSTRACT

A method for coupling transcription and translation from DNA using a solution comprising a eukaryotic cell-free extract comprising adding a sufficient amount of a magnesium compound to the extract to raise the magnesium concentration to a level where RNA is transcribed from DNA and RNA translates into protein.

17 Claims, No Drawings

COUPLED TRANSCRIPTION AND TRANSLATION IN EUKARYOTIC CELL-FREE EXTRACT

This is a continuation of application Ser. No. 08/149,715 filed Nov. 9, 1993, entitled "COUPLED TRANSCRIPTION AND TRANSLATION IN EUKARYOTIC CELL-FREE EXTRACT" now U.S. Pat. No. 5,329,637.

BACKGROUND OF THE INVENTION

This invention relates generally to molecular biology, and more particularly, to a new method allowing coupling of the transcription of RNA from a template DNA and the translation of the RNA in eukaryotic cellular lysates or other extracts.

The steps involved in the transcription and translation (expression) of genes in cells are very complex and are not yet completely understood. There is a basic pattern that must be followed, however, for protein to be produced from DNA. The DNA is first transcribed into RNA, and then the RNA is translated by the interaction of various cellular components into protein. In prokaryotic cells (bacteria) transcription and translation are "coupled", meaning that RNA is translated into protein during the time that it is being transcribed from the DNA. In eukaryotic cells (animals, plants) the two activities are separate, making the overall process much more complicated. DNA is transcribed into RNA inside the nucleus of the cell, but the RNA is further processed into mRNA and then transported outside the nucleus to the cytoplasm where it is translated into protein.

The ability of molecular biologists to isolate and clone genes, as well as their ability to isolate particular mRNAs or "messages" from cells, has brought about the need for systems which can be used to express these genes or messages. The expression of a gene is important in the overall understanding of its function and regulation. Methods are now available for rapid expression of proteins, making it possible to manipulate genes and then study the effect of the manipulations on their function. The amount of protein to be produced, whether the gene is prokaryotic or eukaryotic and the relative merits of an in vitro cell-free or an in vitro whole-cell system, are some of the factors considered by researchers when selecting an expression system. The choice of a system is influenced by the gene being studied. For the most part, a prokaryotic gene is expressed best in a prokaryotic system, and a eukaryotic gene is more efficiently and accurately expressed in a eukaryotic system. This is because of the many regulatory sequences and promoters that are recognized more efficiently in a like system. The expression of genes can be achieved in both in vitro whole-cell and in vitro cell-free systems.

In vitro transcription systems using prokaryotic or eukaryotic cells are available, however, these systems are difficult to work with since intact cells are used. In vitro cell-free systems, on the other hand, are made from cell-free extracts produced from prokaryotic or eukaryotic cells that contain all the necessary components to translate DNA or RNA into protein. Cell-free extracts can be prepared from prokaryotic cells such as E. coli and from eukaryotic cells such as rabbit reticulocytes and wheat germ. Cell-free systems are very popular because there are standard protocols available for their preparation and because they are commercially available from a number of sources.

E. coli S30 cell-free extracts were first described by Zubay, G. (1973, Ann. Rev. Genet. Vol 7, p. 267). These can be used when the gene to be expressed has been cloned into a vector containing the appropriate prokaryotic regulatory sequences, such as a promoter and ribosome binding site. Prokaryotic E. coli cell-free systems are considered "coupled" because transcription and translation occur simultaneously after the addition of DNA to the extract. The use of RNA as a template in E. coli extracts results in protein production but such a reaction is not coupled. Rabbit reticulocyte lysates and wheat germ extracts are used preferably for the expression of eukaryotic genes or mRNA. Both systems require the use of RNA as the template for protein translation because, as previously mentioned, eukaryotic systems are not coupled.

Rabbit reticulocyte lysate was described by Pelham, H. R. B. and Jackson, R. J. (1976, Eur. J. Biochem. Vol. 67, p. 247). This expression system is probably the most widely used cell-free system for in vitro translation, and is used in the identification of mRNA species, the characterization of their products, the investigation of transcriptional and translational control. Processing events, such as signal peptide cleavage and core glycosylation, are examined by adding canine microsomal membranes to a standard translation reaction (Walter, P. and Biobel, G. (1983) Meth. Enzymol. 96, 84). Rabbit reticulocyte lysate also contains a variety of post-translational processing activities, including acetylation, isoprenylation, proteolyis and some phosphorylation activity (Glass, C. A. and Pollard, K. M. (1990) Promega Notes 26).

Wheat germ extract was described by Roberts, B. E. and Paterson, B. M. (1973, Proc. Natl. Acad. Sci. USA, Vol. 70, P. 2330). Cell-free extracts of wheat germ support the translation in vitro of a wide variety of viral and other prokaryotic RNAs, as well as eukaryotic mRNAs. (Anderson, C., et al. (1983) Meth. Enzymol. 101, 635). Generally, it is found necessary to include a ribonuclease inhibitor in the reaction mix of a wheat germ translation system, as ribonuclease activities in wheat germ extract are present.

RNA for translational studies is obtained by either isolating mRNA or by making in vitro RNA transcripts from DNA that has been cloned into a vector containing an RNA polymerase promoter. The first method isolates mRNA or "message" directly from cells.

The second obtains RNA for in vitro translation by in vitro transcription. In vitro transcription of cloned DNA behind phage polymerase promoters was described by Krieg, P. and Melton, D (1984, Nucl. Acids Res., Vol. 12, p. 7057). This has become a standard method for obtaining RNA from cloned genes for use in in vitro translation reactions. This method requires that the DNA or gene of interest be cloned into a vector containing a promoter for one of the following RNA polymerases, SP6, T7 or T3. The vector is then linearized at the 3' end of the cloned gene using a restriction enzyme, followed by an in vitro transcription reaction to make RNA transcripts. A number of vectors containing the SP6, T7 and T3 RNA polymerase promoters are commercially available and are widely used for cloning DNA.

In any case, the process of obtaining RNA transcripts for use in rabbit reticulocyte lysate or wheat germ systems introduces a variable which can affect the efficiency of the translation reaction. Extra care must always be taken when working with RNA as it is easily degraded by ribonucleases. DNA templates are much more stable.

After rabbit reticulocyte lysate and wheat germ extract were developed as cell-free translation systems, attempts were made to couple transcription and translation. One system that was developed was a "linked" transcription and translation system (Roberts, B. E., et al. (1975), *Proc. Natl. Acad. Sci. USA,* Vol 72, 1922–1926). This system involved the use of wheat germ extract and looked at transcription and translation of SV40 viral DNA using *E. coli* RNA polymerase. In this system transcription occurs in 15 minute incubation step Just prior to the addition of the wheat germ extract. The steps are separated because of incompatibility between the buffer conditions necessary for transcription and those necessary for translation, and also because of the different temperature requirements for both processes. This system has a number of drawbacks. One is the lack of control over which protein product is produced, as a number of different proteins are synthesized simultaneously from the same SV40 DNA template. Although the authors of that study indicated that a coupled system had been developed no data for a coupled system was shown.

Another system was developed by Pelham, H. R. B, et al. (1978), *Eur. J. Biochem.,* Vol. 82, 199–209, where coupled transcription and translation occurred after the introduction of vaccinia viral core particles into rabbit reticulocyte lysate. The production of vaccinia proteins from the viral DNA was presumably due to transcription by the endogenous vaccinia RNA polymerase and subsequent translation by the lysate. This system was limited by the fact that only vaccinia proteins would be produced while exogenous DNA from sources other than vaccinia would not be recognized by the RNA polymerase and therefore no transcription or translation could occur. Viral core particles had to be isolated, and the authors were unable to exclusively produce a single protein.

Work has also been described using "continuous" cell-free in vitro translation systems with the emphasis on large scale production of protein. Continuous systems are very different than the more common batch type, or static, in vitro cell-free translation reactions which occur in a contained reaction volume. Continuous translation involves a bioreactor (such as an Amicon 8MC ultrafiltration unit) in which large scale reactions are set up and protein is "continually" translated over extended periods of time. The reaction requires that a buffer be fed into the reaction as it progresses, and also requires that the products of translation be removed from the reaction filter unit. This type of system works well with *E. coli* S30 extract and wheat germ extract when RNA template is introduced. See Spirin, et al. (1988) *Science,* Vol 242, 1162–1164. The system also works using RNA templates in rabbit reticulocyte lysate. See Ryabova, et al. (1989) *Nucl. Acid Res.,* Vol. 17, No. 11, 4412. The system is also known to work well with DNA templates in *E. coli* S30 extracts. See Baranov, et al. (1989) *Gene,* Vol 84, 463–466. PCT publication WO9102076 discloses continuous cell-free translation from DNA templates using eukaryotic lysates.

Continuous reactions are performed variously from tens of hours up to around one hundred hours, and require a substantial investment of time and resources to set up and run. Translation in a "continuous" system is also directed towards producing large amounts of protein, and differs substantially from standard (static) in vitro translation reactions. Static reactions can be run in a small reaction volume, typically measured in microliters, and are often completed in one to two hours. A static translation reaction is not directed towards producing preparative amounts (milligrams) of proteins. A static reaction is generally used to produce protein for investigative applications, such as the identification and characterization of mRNA species, or studies of transcriptional or translation control. None of the rabbit reticulocyte or wheat germ systems currently known for in vitro translation provide for coupled transcription and translation in a static reaction mixture.

SUMMARY OF THE INVENTION

It is an object of the invention, therefore, to provide a simple method for producing protein from a template DNA in a standard in vitro translation reaction utilizing a eukaryotic cellular lysate.

A more specific object of the invention is to provide such a method which can be used to couple transcription and translation of a single protein coded by the DNA template.

Another object is to provide a process for enhanced in vitro protein production from DNA templates through coupled transcription and translation reactions using eukaryotic cell-free lysates.

A further object is to provide a method for manufacturing eukaryotic cellular lysates for use in coupled transcription and translation experiments.

A still further object is to provide a method for producing such a lysate preparation which has one or more of the components or reagents necessary for coupled transcription and translation.

It is another object to provide such a preparation for use in coupled transcription and translation experiments.

A further object of the invention is to provide a kit having a prepared rabbit reticulocyte lysate or wheat germ extract and including other components or reagents necessary for producing a reaction mixture for coupling transcription and translation from a DNA template.

A more specific object is to provide a kit having as at least one component a prepared rabbit reticulocyte lysate or wheat germ extract preparation which has one or more of the reagents necessary for coupling transcription and translation.

For the achievement of these and other objects, this invention provides a method for coupling transcription and translation in eukaryotic cellular lysate. The method comprises adding a sufficient amount of a magnesium compound to the lysate to raise the final magnesium concentration thereof to a level where RNA is transcribed from DNA and RNA translates into protein.

The invention also provides a process for producing protein from a DNA template having a specific polymerase promoter sequence through coupled transcription and translation in a solution. This is accomplished by preparing a standard preparation of a eukaryotic cellular lysate, modifying the lysate with sufficient concentrations of ribonucleotide triphosphates, amino acids and the polymerase corresponding to the promoter sequence of the template DNA to support transcription and translation, and adding a sufficient amount of a magnesium compound to the solution to raise the final magnesium concentration to a level where RNA is transcribed from DNA and RNA translates into protein. Only that protein corresponding to the gene adjacent the promoter sequence in the DNA will be produced.

The invention additionally provides a modified eukaryotic cellular lysate prepared in accordance with the method whereby the final magnesium concentration is raised to a level where RNA is transcribed from DNA and RNA translates into protein. The lysate can have its magnesium concentration so adjusted during manufacture. The invention also provides a kit that comprises a container containing prepared eukaryotic cellular lysate for coupled transcription and translation. In addition to having an adjusted magnesium concentration, this lysate can contain a variety of additional components required for coupled transcription and translation. One of the additional components that can be included is an RNA polymerase. Others are various buffers or salts or other components or reagents for optimizing coupled transcription and translation reaction conditions, such as spermidine, which is known to stimulate the efficiency of chain elongation.

The coupling of transcription and translation in rabbit reticulocyte or wheat germ systems significantly increases protein production when compared to standard in vitro translation with RNA templates, and the coupled transcription and translation has been shown to work for a variety of different proteins over a wide range of molecular weight sizes.

The gene or DNA to be translated is preferably cloned behind an RNA polymerase promoter such as the SP6, T7, or T3 promoters, or any RNA polymerase promoter for which a polymerase is available. The DNA template can be introduced into the coupled transcription and translation reaction in the form of a closed circular plasmid DNA or as a linearized plasmid DNA. RNA polymerase promoter sequences can also be attached to specific DNA fragments by the thermocycling amplification process, and these linear DNA fragments can be used in coupled transcription and translation reactions.

Standard in vitro translation reactions require very little investment of time and resources and are a well established method for expressing protein qualitatively. By coupling transcription and translation in standard in vitro translation reactions using rabbit reticulocyte lysate or wheat germ extract the need for a separate in vitro transcription reaction is eliminated and protein production is significantly enhanced. Thus, coupled transcription and translation using rabbit reticulocyte lysate or wheat germ extract provides a significant improvement over current standard in vitro translation reactions. An unexpected benefit is that the production of the desired protein product is increased dramatically (several fold) over that which is seen by the addition of RNA to standard in vitro translation reactions. In addition, there is no need for a separate capping reaction with coupled transcription and translation.

Another advantage is that protein production can be achieved from a cloned or amplified DNA template containing a specific RNA polymerase promoter. In this manner RNA can be directed to be synthesized from a single gene downstream of the promoter, and only the proteins translated from that RNA are produced. If that RNA directs only one protein, then only one protein is produced through the reaction. Plasmid vectors for such use are well known in the art and are available from several sources, allowing the researcher to produce protein from any cloned gene at will.

Other features and advantages of the invention will become apparent to those of ordinary skill in the art upon review of the following detailed description and claims.

DESCRIPTION OF THE PREFERRED EMBODIMENT

For purposes of the invention, any eukaryotic cellular lysate can be used, and a number of conventional techniques exist for their preparation. Eukaryotic cell-free lysates are preferred expression systems for many reasons, at least partially because they retain a variety of post-translational processing activities. With the addition of canine microsomal membranes processing events, such as signal peptide cleavage and core glycosylation, can be examined. Eukaryotic cellular lysates also support the translation in vitro of a wide variety of viral and other prokaryotic RNAs, as well as eukaryotic mRNAs.

While other eukaryotic systems are suitable, rabbit reticulocyte lysate and wheat germ extract are preferred. These eukaryotic lysates are popular with researchers, and are widely available. In a preferred embodiment, rabbit reticulocyte lysate is prepared by a method described by Pelham, H. and Jackson, R. J. (1976, *Eur. J. Biochem.* 67, 247–256) and modified according to the manufacturing protocol L415/L416, Promega Corp., Madison, Wis. Reticulocyte lysate is prepared from New Zealand White rabbits injected with phenylhydrazine, which ensures reliable and consistent reticulocyte production in each lot. The reticulocytes are purified to remove contaminating cells which could otherwise alter the translational properties of the final extract. After the reticulocytes are lysed, the extract is treated with micrococcal nuclease and $CaCl_2$, to destroy endogenous mRNA and thus reduce background translation to a minimum. EGTA is then added to chelate the $CaCl_2$ and thereby inactivate the nuclease.

The lysate contains cellular components necessary for protein synthesis. These include tRNAs, rRNAs, amino acids and initiation, elongation, and termination factors. The lysate is further optimized for mRNA translation by adding an energy generating system, consisting of pre-tested phosphocreatine kinase and phosphocreatine. Also added are a mixture of tRNAs to expand the range of mRNAs which can be translated, and hemin to prevent inhibition of initiation. Hemin is included in the reticulocyte lysate because it is a suppressor of an inhibitor of the initiation factor $eIF2\alpha$. In the absence of hemin, protein synthesis in reticulocyte lysates ceases after a short period of incubation (Jackson, R. and Hunt, T. 1983 *Meth. In Enzymol.* 96, 50). Potassium acetate and magnesium acetate are added at a level recommended for the translation of most mRNA species. This is the standard rabbit reticulocyte lysate used for in vitro translations. The final magnesium concentrations for standard rabbit reticulocyte lysate, are typically in the range of about 4.2 to 5.0 mM, which is used at a 50% ratio in coupled transcription and translation reactions.

| Final Concentration Contributions of Added Components in a Rabbit Reticulocyte Lysate Translation Reaction Which is 50% Lysate | |
|---|---|
| Creatine phosphate | 7 mM |
| Creatine phosphokinase | 35 µg/ml |
| DTT | 1.4 mM |
| Calf liver tRNA | 35 µg/ml |
| Potassium acetate | 56 mM |
| Magnesium acetate | 350 µM |
| Hemin | 14.3 µM |

Another preferred embodiment utilizes wheat germ extract. This can be prepared by a method described by Roberts, B. E. and Paterson, B. M. (1973), *Proc. Natl. Acad. Sci. USA* Vol. 70, No. 8, pp. 2330–2334), following the modifications described by Anderson, C. W., et al. (1983, *Meth. Enzymol.* Vol. 101, p. 635) and modified as in the manufacturing protocol L418, Promega Corp. Madison, Wis. Generally, wheat germ extract is prepared by grinding wheat germ in an extraction buffer, followed by centrifugation to remove cell debris. The supernatant is then separated by chromatography from endogenous amino acids and plant pigments that are inhibitory to translation. The extract is also treated with micrococcal nuclease to destroy endogenous mRNA, to reduce background translation to a minimum. The extract contains the cellular components necessary for protein synthesis, such as tRNA, rRNA and initiation, elongation, and termination factors. The extract is further optimized by the addition of an energy generating system consisting of phosphocreatine kinase and phosphocreatine, and magnesium acetate is added at a level recommended for the translation of most mRNA species. The final magnesium concentration for standard wheat germ extract, is typically in the range of about 6.0 mM to 7.5 mM.

| Final Concentration Contributions of Added Components in a Wheat Germ Extract Translation Reaction Which is 50% Extract | |
| --- | --- |
| Creatine phosphate | 10 mM |
| Creatine phosphokinase | 50 μg/ml |
| DTT | 5 mM |
| Calf liver tRNA | 50 μg/ml |
| Magnesium acetate | 3.0–3.75 mM |
| Potassium acetate | 50 mM |
| Spermidine | 0.5 mM |
| ATP | 1.2 mM |
| GTP | 0.1 mM |
| HEPES (pH 7.6) | 12 mM |

For coupled transcription and translation the magnesium concentration of the eukaryotic cellular lysate must be adjusted by an additional magnesium compound, preferably a salt. Preferred salts include magnesium chloride and magnesium acetate. The addition of a buffering agent can be used in the solution to stabilize the pH, although this isn't necessary. For coupling transcription and translation, a sufficient amount of magnesium chloride or acetate is added to the lysate to raise the final magnesium concentration to a level where RNA is transcribed from DNA and RNA translates into protein. This level will vary depending upon the lysate used.

The simple addition of a prokaryotic RNA polymerase and ribonucleotide triphosphates to a standard rabbit reticulocyte lysate or wheat germ extract does not allow in vitro protein production from DNA templates. The particular adjustments of the salt concentrations in the system that will be described, however, allow protein production by creating conditions within the lysate which permit both transcription of DNA into RNA and translation of the RNA into protein.

Magnesium is known to be important for optimizing translation, as it enhances the stability of assembled ribosomes and functions in their binding together during translation. Magnesium also appears to play a role in facilitating polymerase binding. Potassium is important as well for optimizing translation, but unlike the case for magnesium, for coupled transcription and translation the concentration of potassium ions does not need to be altered beyond standard translation preparation levels.

Potassium and magnesium are in the standard rabbit lysate. The levels are partially from the endogenous lysate levels, and partially from the additions made in the preparation of the lysate, as are done for translation lysates. Lysate is diluted somewhat in manufacture, and the prepared lysate is then only used at 50% for coupled transcription and translation reactions.

As the magnesium concentration should be adjusted to within a rather narrow optimal range, it is preferred that the lysate magnesium levels be measured directly through the use of a magnesium assay, prior to the addition of extra magnesium, so that the amount of magnesium in a reaction can be standardized from one batch of lysate to the next. The Lancer "Magnesium Rapid Stat Diagnostic Kit" (Oxford Lab Ware Division, Sherwood Medical Co., St. Louis, Mo.), is one such assay which can accurately measure the magnesium levels in biological fluid. Once the magnesium ion concentration for a given batch of lysate is known then additional magnesium, for instance in the form of a concentrated magnesium salt solution, can be added in a known manner to bring the magnesium concentration of the lysate to within the optimal range, or, in the case of a modified lysate preparation to be used as one-half of a reaction mixture, to within twice the optimal range.

Thus, it has been found that when the final magnesium concentration of rabbit reticulocyte lysate is adjusted, such as by adding a concentrated solution of magnesium chloride or acetate, to a concentration greater than 2.5 mM but less than 3.5 mM, preferably between 2.6 mM and 3.0 mM, coupled transcription and translation occurs. For coupling transcription and translation using wheat germ extract, a final concentration of magnesium chloride or acetate greater than about 3.0 mM but less than about 5.25 mM produces protein, preferably adjusted to approximately 4.0 mM to 4.75 mM.

Reaction conditions for coupled transcription and translation must include the addition of ribonucleotide triphosphates (ATP, GTP, CTP, UTP) and amino acids, for rabbit reticulocyte lysate to final concentrations of 0.4 mM each, and 20 μM each respectively. Reaction conditions for wheat germ extract are modified by the addition of ribonucleotide triphosphates to final concentrations of 0.4 mM for CTP and UTP, 0.5 mM for GTP and 1.6 mM for ATP, while amino acids are added to a final concentration of 20–80 μM. If a radiolabeled amino acid is used in the coupled reaction, such as $^{35}$S methionine or $^3$H leucine, then the corresponding amino acid is left out of the amino acid mix. An RNA polymerase, either SP6, T7, or T3, is then added, preferably to a final concentration of about 80–160 units per 50 μl reaction. The DNA template with the gene to be translated is added at a concentration of 1 μg, and the reaction volume is adjusted to 50 μl with the addition of water. The reaction is then incubated at 30° C. for 1–2 hours.

Although potassium is added to the reaction mixture in the preferred embodiment, in contrast to magnesium additional potassium does not greatly increase protein production, but only offers a slight improvement when proper magnesium levels are already present. Potassium acetate is added to an optimal final concentration of about 59 mM. Although potassium chloride or acetate can be added, because of the greater amounts added than is the case for magnesium, potassium acetate is preferred. The standard translation lysate level can be used, a concentration of approximately 56 mM, while spermidine is added to give a final concentration of about 0.2 mM. The final concentration of potassium chloride or acetate is also an estimation based on the amount of this component in standard lysate, but it must be recognized that this concentration, as well as the magnesium concentration, can vary slightly due to endogenous components.

Additional components can be added to the lysate as desired for improving the efficiency or stability of the coupled transcription and translation reaction. One common addition to coupled transcription and translation reactions is an amount of a polyamine sufficient to stimulate the efficiency of chain elongation. Although not absolutely necessary, for coupled transcription and translation a final concentration of spermidine in the mixture of about 0.2 mM is optimal, in that an increase of protein production is observed with this concentration. Polyamines affect optimal magnesium levels as well, and are known to lower the effective magnesium concentration for translation reactions somewhat. It appears that the polyamines may substitute for magnesium at some level, and thus would play a role in the optimization of magnesium requirements, possibly even permitting some lowering of optimal magnesium levels for coupled transcription and translation.

Optimal magnesium concentrations in the in vitro environment are affected by other conditions and considerations, too. As the ribonucleotide triphosphate concentration goes up, for instance, there is a concomitant increase in the optimal magnesium concentration, as the ribonucleotide triphosphates tend to associate, or chelate, with magnesium in solution. Thus, when the ribonucleotide triphosphate concentrations cited for the above reactions are increased to 0.6 mM, the production of protein from coupled transcription and translation reactions is greatly reduced. The optimal concentration of magnesium also varies with the type of cellular lysate, whether using wheat germ extract or rabbit reticulocyte lysate. The amount of magnesium required to be added to achieve optimal levels will vary with the concentration of the lysate used in the reaction mixture, as increasing the concentration of the lysate will increase the contribution of magnesium from the lysate itself.

Due to the large number of components in a lysate mixture, it can not be said with certainty whether it is the protein translation from RNA, the transcription of RNA from DNA or both that is adversely affected at other than optimal salt conditions. The observation is the same in any case, that detectible levels of protein are not produced in the reaction. With a small adjustment to the magnesium concentration, possibly adjusted by the polyamine concentration and watching that ribonucleotide triphosphate concentration levels do not become a problem, coupled transcription and translation is observed, but only through a relatively small range.

Dithiothreitol (DTT) is preferably added to the translation mixture. When included in coupled transcription and translation reactions, DTT is preferably added to a final concentration of about 1.45 mM. Optimal DTT is about 5.1 mM for wheat germ. Also, a ribonuclease inhibitor, such as RNasin, can be added to the lysate, to effectively inactivate endogenous ribonucleases. Concentrations of 40 units per 50 μl reaction have been shown to help prolong the reaction. It is not an absolute requirement for coupled transcription and translation in rabbit reticulocyte lysate, but RNasin is required for coupled transcription and translation using wheat germ extract. The omission of RNasin from the latter results in no protein translation, as there are active ribonucleases present in the lysate.

The preferred coupled transcription and translation concentrations for rabbit reticulocyte lysate, of potassium chloride or acetate, magnesium chloride or acetate and spermidine, can be achieved by the addition of 2.5 μl of an optimized tris/acetic acid buffer (1×TA buffer=33 mM Tris/acetic acid ph 7.8, 65 mM potassium acetate, 10 mM magnesium acetate, 4 mM spermidine, 1 mM DTT). When added to a standard 50 μl in vitro translation reaction, this buffer raises the magnesium level in the lysate by 0.5 mM overall.

Rabbit reticulocyte lysate can be modified during manufacture. The lysate is used at a 50% concentration (25 μl lysate per 50 μl reaction, typically), and so a preferred modification involves adjusting the potassium acetate concentration to 118 mM, the magnesium acetate to about 5.2 mM to 6.0 mM, and spermidine to 0.4 mM. This gives optimal final concentrations of 59 mM potassium acetate, 2.6 mM to 3.0 mM magnesium acetate and 0.2 mM spermidine when 50% lysate is used in a coupled transcription and translation reaction. The lysate can be further modified by the addition of one of the RNA polymerases (SP6, T7, or T3) to the lysate, preferably at a concentration of 80–160 units per 50 μl reaction. Such a modified lysate can be stored frozen until needed.

Spermidine is also preferably added to wheat germ extract, optimally to a final concentration of about 0.9 mM. Potassium acetate is preferably added to a final concentration of approximately 56.5 mM. These concentrations can be achieved by the addition of 5.0 μl of 1×TA buffer to a 50 μl in vitro translation using standard wheat germ extract, although these concentrations are based on estimations of the amounts of these components in standard wheat germ extract and may vary slightly due to endogenous components in the lysate itself.

Wheat germ extract can also be modified during the manufacturing process so that the final concentrations of potassium acetate, magnesium acetate and spermidine will equal those described in the reaction conditions above for wheat germ when the lysate is used at a 50% concentration. Wheat germ extract can be further modified during manufacture by the addition of one of the RNA polymerases to a final concentration of 80–160 units per reaction. Modified extract is stored frozen until it is used.

Leaving magnesium concentrations at levels present in the standard lysate, production of protein does not occur. The addition of all of the other components of the 1×TA buffer to the reaction mixture, only without the magnesium, results in a reaction that produces no protein. On the other hand, addition of excess magnesium will cease translation altogether. For instance, in a similar reaction mixture utilizing rabbit reticulocyte lysate, but having final magnesium concentrations of about 3.5 mM, translation of protein again ceases. This upper limit will presumably vary slightly depending upon other parameters such as potassium and spermidine concentrations, as well as ribonucleotide triphosphate concentrations both of which are known to vary the optimal magnesium concentration for translation of RNA into proteins.

Both modified wheat germ extract and modified rabbit reticulocyte lysate can be included as part of a kit for facilitating the set up of coupled transcription and translation reactions. Such a kit improves the convenience to the researcher, as the eukaryotic cellular lysate comes prepared and ready for use. In addition to the rabbit reticulocyte lysate or wheat germ extract, such a kit can include the components, reagents, including enzymes, and buffers necessary to perform coupled transcription and translation upon the introduction of a DNA template. The lysate can be standard, or can be of the type where the adjustments to its salt concentrations have already been made during manufacture, or additionally where one or more of the components, reagents or buffers necessary for coupled transcription and translation have been included.

The amount of protein produced in a coupled in vitro transcription and translation can be measured in various fashions. One method relies on the availability of an assay which measures the activity of the particular protein being translated. An example of an assay for measuring protein activity is the luciferase assay system described in Technical Bulletin 101, Promega Corp., Madison, Wis. These assays measure the amount of functionally active protein produced from the coupled in vitro transcription and translation reaction. Activity assays will not measure full length protein that is inactive due to improper protein folding or lack of other post translational modifications necessary for protein activity.

Another method of measuring the amount of protein produced in coupled in vitro transcription and translation reactions is to perform the reactions using a known quantity of radiolabeled amino acid such as $^{35}S$ methionine or $^{3}H$ leucine and subsequently measuring the amount of radiolabeled amino acid incorporated into the newly translated protein. For a description of this method see the in vitro Translation Technical Manual, Promega Corp., Madison, Wis. Incorporation assays will measure the amount of radiolabeled amino acids in all proteins produced in an in vitro translation reaction including truncated protein products. It is important to separate the radiolabeled protein on a protein gel, and by autoradiography confirm that the product is the proper size and that secondary protein products have not been produced. The most accurate measure of protein production is to correlate the measure of activity with the measurements of incorporation.

As described above, coupled transcription and translation reactions require the introduction of a DNA template. Further enhancement of in vitro protein translation has been achieved with the use of a vector containing a poly A sequence at one end of the multiple cloning region. A preferred vector also contains an SP6, T7 or T3 RNA polymerase promoter at the opposite end of the multiple cloning region, so that cloning into the vector produces a gene that is flanked by an RNA polymerase promoter at the 5' end and a poly A sequence at the 3' end. Many cloning vectors commercially available contain one or more of the promoters SP6, T7, or T3 as they are widely used for standard in vitro transcription reactions. The vector pSP64 (poly A) is commercially available from Promega Corp., Madison, Wis. This vector was used to clone the luciferase gene which was subsequently translated in a coupled transcription and translation reaction using rabbit reticulocyte lysate. The same luciferase gene was cloned into a different vector lacking the poly A sequence and subsequently translated in a coupled transcription and translation reaction. When activity assays were performed on product from these reactions, a significant increase in activity was evident in the reaction which contained the poly A construct.

To study the cotranslational and initial post-translational modifications of proteins, coupled transcription and translation reactions can be performed in the presence of canine pancreatic microsomal membranes. Signal peptide cleavage, membrane insertion, translocation and core glycosylation are some of the modifications that can be studied. A coupled transcription and translation reaction using a clone of the B-lactamase precursor in the presence of microsomal membranes produced the expected form of the protein showing signal processing had taken place. Likewise, a coupled transcription and translation reaction using a clone of the precursor for α factor from S. cerevisiae in the presence of microsomal membranes produced the expected processed form of the protein showing glycosylation.

Coupled transcription and translation can be used in any method that requires the in vitro translation of proteins. These methods include in vitro mutagenesis of genes to study structure and function of the resulting proteins. Other methods are the in vitro translation of modified proteins for the purpose of isolating or purifying the protein away from the rest of the reaction and the in vitro translation of protein for the purpose of producing antibodies to that protein. The method of coupled transcription and translation in rabbit reticulocyte lysate or wheat germ extract offers advantages over current methods of in vitro translation in that these systems require less time and yield enhanced levels of protein.

There are also a number of advantages in using such a static coupled transcription and translation reaction over continuous or flow-through reactions. First of all, there is a major difference in the applications for the two systems. The continuous system is for large scale industrial production of proteins whereas static system reactions are suited to the everyday researcher currently doing in vitro translations. Continuous translation is much more expensive to perform, requiring an investment in equipment (a single Amicon unit costs approximately $2,000) as well as significant amounts of reagents. In particular, the levels of RNA polymerases used to make continuous eukaryotic reactions work is prohibitive for simple research applications (20,000–30,000 units/reaction). Continuous reactions are designed to be performed in relatively large volumes, while static reactions require no extra equipment and only small amounts of reagents, since the reaction volume is typically only on the order of 50 µl or less.

The time required for a continuous reaction is significant, anywhere from 24 to 100 hours, whereas static reactions require only 1 to 2 hours to completion. For researchers currently performing in vitro translation, the static system offers significant time savings for most analytical or other research applications by bypassing the in vitro transcription step. Because of the time required both for the set up and for the running of continuous reactions there is no net time savings for a typical researcher, even for coupled translation and transcription in such a system. Furthermore, with the static coupled transcription and translation system significant increases in protein production are observed when compared to standard in vitro translation using RNA templates. Further increase in protein production is observed in the static system when the DNA template contains a 3' poly A sequence.

In general, then, the static system makes coupled transcription and translation available to the everyday researcher, not only because of the cost effectiveness and ease of use, but also because of the significant time savings and increased protein production over other known eukaryotic systems.

EXAMPLE 1

Coupled transcription and translation was performed on a DNA construct containing the luciferase gene. The reaction was assayed for the production of luciferase enzyme using the luciferase assay system (Promega, Corp., Madison, Wis). Luciferase activity is measured in Turner light units using a Turner luminometer. Coupled transcription and translation was achieved under the following reaction conditions:

| | |
|---|---|
| 25.0 µl | standard rabbit reticulocyte lysate |
| 8.0 µl | rNTP's (ATP, GTP, UTP, CTP) 2.5 mM each |
| 1.0 µl | SP6 RNA polymerase (80 units/µl) |
| 2.5 µl | 1xTA buffer* |
| 1.0 µl | RNasin (40 units/µl) |
| 1.0 µl | pSP64polyA/luc DNA (1 µg) circular plasmid DNA |
| 1.0 µl | 1 mM amino acids (complete) |
| 9.5 µl | H$_2$O |
| 50.0 µl | |

*1xTA buffer consists of 33 mM Tris/acetic acid Ph 7.8, 65 mM potassium acetate, 10 mM magnesium acetate, 4 mM spermidine, and 1 mM DTT.

The reaction was incubated at 30° C. for 1.5 hours. After 1.5 hours a 2.5 μl sample from the above reaction was assayed in the luminometer with a 100× light filter in place. The sample produced greater than 30,000 Turner light units. Control experiments where either DNA was omitted from the reaction or where no 1×TA was included produced no Turner light units.

EXAMPLE 2

Coupled transcription and translation was likewise performed in a reaction containing wheat germ extract. Again, the DNA construct used contained the luciferase gene. Coupled transcription and translation was achieved under the following conditions:

| | |
|---|---|
| 25.0 μl | standard wheat germ extract |
| 8.0 μl | rNTP's (ATP, GTP, CTP, UTP) 2.5 mM each |
| 5.0 μl | 1×TA buffer |
| 1.0 μl | RNasin (40 units/μl) |
| 1.0 μl | SP6 RNA polymerase (80 units/μl) |
| 1.0 μl | pSP64polyA/luc DNA (1 μg) circular plasmid DNA |
| 1.0 μl | 1 mM amino acids (complete) |
| 8.0 μl | H$_2$O |
| 50.0 μl | |

The reaction was incubated for 1 hour at 30° C. After 1 hour a 2.5 μl sample from the reaction was measured in the luminometer with a 100× light filter in place. The sample produced greater than 5,000 Turner light units.

EXAMPLE 3

Coupled transcription and translation was also performed with lysates modified during manufacture by the addition of certain components or reagents. During the manufacture of a rabbit reticulocyte lysate an aliquot was set aside and SP6 RNA polymerase was added to the lysate before it was frozen. SP6 was added to the level of 160 units of SP6 per 25 μl lysate. The lysate was quick frozen and stored at −70° C. until used. Coupled transcription and translation reactions were set up following conditions in example 1 except that no additional SP6 was added. The reactions performed with rabbit reticulocyte lysate that had SP6 RNA polymerase added during manufacture produced protein. Further experiments have shown that the other components (buffers and amino acids, for instance) necessary for coupled transcription and translation can be added to the lysate during its manufacture. The lysate with the components added can be used to produce protein in coupled reactions upon the introduction of DNA templates.

EXAMPLE 4

DNA constructs containing genes for a variety of proteins were tested in coupled transcription and translation reactions. The same reaction conditions as in example 1 were used except that a radiolabeled amino acid ($^{35}$S methionine) was included in the reaction mix. Methionine was eliminated from the amino acid mix. Reactions were performed using plasmid DNA constructs cloned behind the SP6 or T7 RNA polymerase promoters. pGEMLuc plasmid DNA coding for luciferase was used in coupled transcription and translation reactions and yielded 15.3% incorporation of the radiolabeled amino acid. This compared to a standard in vitro translation using a transcribed RNA template of the luciferase clone which yielded 0.8% incorporation. Samples from these reactions were run on SDS/PAGE gels to confirm that the protein product was the proper size for luciferase. Further experiments were performed using a clones of the B-lactamase gene and the α factor of *S. cerevisiae* behind the SP6 promoter. Standard in vitro translation using an RNA template of B-lactamase yielded 3% incorporation of the labeled amino acid whereas a coupled transcription and translation reaction using a DNA template yielded 26.8% incorporation. A standard in vitro translation reaction using an RNA template of the α factor gene yielded 0.8% incorporation while a coupled transcription and translation reaction using a DNA template yielded 12.4% incorporation. Again, samples of the reactions were run on SDS/PAGE gels to confirm the size of the proteins produced. Other proteins produced from DNA templates in coupled transcription and translation reactions include: TFIID transcription factor, behind the T7 promoter, yielding 5% incorporation; CJun transcription factor, behind T7, yielding 13.4% incorporation; B-galactosidase, behind the SP6 promoter, yielding 28% incorporation; and polyA/luc, a luciferase gene in a poly A vector, behind SP6, yielding 25.9% incorporation.

EXAMPLE 5

Coupled transcription and translation was performed in rabbit reticulocyte lysate using a DNA construct of B-lactamase precursor, in the presence and absence of canine microsomal membranes, to test post-translational modification of proteins. The reactions contained a labeled amino acid in order to visualize the products by autoradiography. Products from the reactions were run on SDS/PAGE gels. The protein product from the reaction without microsomal membranes migrated at about 31.5 kilodaltons (Kd) while the protein product from the reaction containing microsomal membranes migrated at about 28.9 Kd, indicating that the signal sequence had been processed.

In a similar coupled transcription and translation experiment a DNA construct of the α factor of *S. cerevisiae* was translated both in the presence and absence of canine microsomal membranes. Again, the radiolabeled products were run on a gel and the results indicated the 18.6 Kd precursor had been processed to a protein migrating at 32.0 Kd, indicating that the αfactor was glycosylated.

EXAMPLE 6

Coupled transcription and translation was performed on DNA produced from a thermocycled amplification process. The only requirement for such a DNA is that the amplified fragment contain an RNA polymerase promoter. The experiment was performed using a DNA fragment amplified from the pGEMLUC plasmid. The resulting fragment contained the sequence for the SP6 RNA polymerase promoter and the sequence for the luciferase gene. When this DNA fragment was introduced into a coupled reaction under conditions similar to example 1, luciferase protein was produced. Other amplified DNA fragments have been translated in coupled reactions including a pGEMEX/gene 10 fragment, behind the T7 promoter, and a B-galactosidase fragment, behind the SP6 promoter.

Although one embodiment of the present invention has been described, it will be apparent to those skilled in the art that various changes and modifications may be made therein without departing from the spirit of the invention or from the scope of the appended claims.

What is claimed is:

1. A method for coupling transcription and translation in a eukaryotic cell-free extract to produce protein in a static reaction comprising the steps of:

adding a DNA template to the extract;

adding ribonucleotides triphosphates to the extract;

adding a RNA polymerase to the extract; and adding a sufficient amount of a magnesium salt to the extract to raise the magnesium concentration to a level where RNA is transcribed from the DNA template and RNA translates into protein.

2. A process for producing protein from a DNA template through coupled transcription and translation in a batch reaction, said process comprising the steps of preparing a eukaryotic cell-free extract, adding to the extract the DNA template, adding to the extract ribonucleotide triphosphates, amino acids and a polymerase, and adding a sufficient amount of a magnesium salt to the extract to raise the final magnesium concentration to a level where RNA is transcribed from the DNA template and RNA translates into protein.

3. The method of claim 1 wherein the RNA polymerase is selected from the group consisting of SP6, T7 and T3 RNA polymerases.

4. The method of claim 1 and further including the step of adding a ribonuclease inhibitor to the extract to inactivate endogenous ribonucleases.

5. The method of claim 1 and further including the step of adding a polyamine to the extract.

6. The method of claim 1 and further including the step of adding potassium to the extract.

7. The method of claim 1 wherein the DNA template has a multiple cloning region, further including the steps of locating a polymerase promotor sequence at one end of the multiple cloning region and a poly A sequence at the opposite end of the multiple cloning region, and wherein the RNA polymerase added to the extract corresponds to the polymerase promotor sequence.

8. The method of claim 2 wherein the RNA polymerase is selected from the group consisting of SP6, T7 and T3 RNA polymerases.

9. The method of claim 2 and further including the step of adding a ribonuclease inhibitor to the extract to inactivate endogenous ribonucleases.

10. The method of claim 2 and further including the step of adding a polyamine to the extract.

11. The method of claim 2 and further including the step of adding potassium to the extract.

12. The method of claim 2 wherein the DNA template has a multiple cloning region, further including the steps of locating a polymerase promotor sequence at one end of the multiple cloning region and a poly A sequence at the opposite end of the multiple cloning region, and wherein the RNA polymerase added to the extract corresponds to the polymerase promotor sequence.

13. A kit for producing protein from a DNA template through coupled transcription and translation, said kit comprising the following components adapted to be used in a batch reaction:

eukaryotic cell-free extract, ribonucleotide triphosphates,

RNA polymerase, and magnesium at a concentration whereby RNA is transcribed from the DNA template and RNA translates into protein.

14. A kit as set forth in claim 5 and further comprising a polyamine.

15. A kit as set forth in claim 5 and further comprising a ribonuclease inhibitor.

16. A kit as set forth in claim 5 and further comprising amino acids.

17. A eukaryotic cell-free extract for producing protein from a DNA template through coupled transcription and translation in a batch reaction, said extract including ribonucleotide triphosphates, RNA polymerase, and a sufficient amount of a magnesium to raise the final magnesium concentration in the extract to a level where RNA is transcribed from the DNA template and RNA translates into protein.

* * * * *

UNITED STATES PATENT AND TRADEMARK OFFICE
CERTIFICATE OF CORRECTION

PATENT NO. : 5,492,817
DATED : February 20, 1996
INVENTOR(S) : David V. Thompson, et al.

It is certified that error appears in the above-indentified patent and that said Letters Patent is hereby corrected as shown below:

On the title page, item [*] Notice: "5,224,637" should be -- 5,324,637--.

Signed and Sealed this

Twenty-third Day of November, 1999

Attest:

Q. TODD DICKINSON

*Attesting Officer*     *Acting Commissioner of Patents and Trademarks*